United States Patent

Schulz

[19]

[11] Patent Number: 5,818,901
[45] Date of Patent: Oct. 6, 1998

[54] MEDICAL EXAMINATION APPARATUS FOR SIMULTANEOUSLY OBTAINING AN MR IMAGE AND AN X-RAY EXPOSURE OF A SUBJECT

[75] Inventor: Reiner Schulz, Dormitz, Germany

[73] Assignee: Siemens Aktiengesellschaft, Munich, Germany

[21] Appl. No.: 921,714

[22] Filed: Sep. 2, 1997

[30] Foreign Application Priority Data

Oct. 9, 1996 [DE] Germany .................. 196 41 628.0

[51] Int. Cl.⁶ .................................................. A61B 5/00
[52] U.S. Cl. .................................. 378/63; 378/4; 600/411
[58] Field of Search ................. 378/63, 4, 193; 600/410, 411

[56] References Cited

U.S. PATENT DOCUMENTS 5,377,678  1/1995  Dumoulin et al. ................... 600/41

FOREIGN PATENT DOCUMENTS

OS 39 31 531  4/1990  Germany .

*Primary Examiner*—Don Wong
*Attorney, Agent, or Firm*—Hill & Simpson

[57] ABSTRACT

A medical diagnostic installation has an MR apparatus and an X-ray exposure apparatus and allows MR exposures and X-ray exposures to be simultaneously produced. A common patient support is provided, so that a patient can be simultaneously charged with magnetic fields and transirradiated by X-rays. The generation of the X-ray images ensues with a solid-state detector.

7 Claims, 2 Drawing Sheets

MEDICAL EXAMINATION APPARATUS FOR SIMULTANEOUSLY OBTAINING AN MR IMAGE AND AN X-RAY EXPOSURE OF A SUBJECT

BACKGROUND OF THE INVENTION

1. Field of the Invention

The present invention is directed to a magnetic resonance imaging apparatus, and in particular to a magnetic resonance imaging apparatus which allows other types of diagnostic exposures of a subject to be obtained in combination with a magnetic resonance image.

2. Description of the Prior Art

Nuclear magnetic resonance imaging (MR) is a proven diagnostic method that enables production of tomograms and three-dimensional reconstructions. X-ray diagnostics, however, is better-suited for image generation for some applications, for example for bone display. When both an MR exposure and an X-ray exposure are to be produced for a patient, it is necessary to place the patient into two different devices. German OS 39 31 531 discloses a medical diagnostic installation having an MR apparatus and an X-ray exposure apparatus wherein the image data are superimposed for improving the diagnosis. An MR exposure and an X-ray exposure for the same patient, however, can only be successively produced.

SUMMARY OF THE INVENTION

An object of the present invention is to provide a medical diagnostic installation wherein MR exposures and X-ray exposures can be simultaneously produced.

The above object is achieved in accordance with the principles of the present invention in a medical diagnostic apparatus having a system for producing a magnetic resonance image as well as an X-ray exposure system, the X-ray exposure system being spatially arranged on the MR apparatus so that X-ray exposures of a patient can be simultaneously produced while obtaining an MR image, with the subject on a single patient support for producing both the X-ray exposure and the MR image. Repositioning of the patient for obtaining the two different images, which can be obtained simultaneously, is not necessary.

The invention is based on the recognition that it is possible to combine an X-ray apparatus and an MR apparatus, despite the difficulty of providing a suitable image detector for the X-ray apparatus in such a combination. If film or foil is provided for producing the X-ray exposures, then real-time operation (simultaneous exposures) is not possible since the films have to be developed first, and storage foils have to be read out first. A real-time-compatible X-ray image intensifier cannot be utilized since the image thereof would be disturbed by the magnetic fields of the MR apparatus. A solid-state detector on the basis of a matrix of detector elements of, for example, amorphous hydrated silicon is utilized as the X-ray exposure system in the invention. This type of detector is free of influence by the magnetic field and enables the registration of X-ray images in real time simultaneously with the registration of MR images.

DESCRIPTION OF THE PREFERRED EMBODIMENTS

Figure 1:
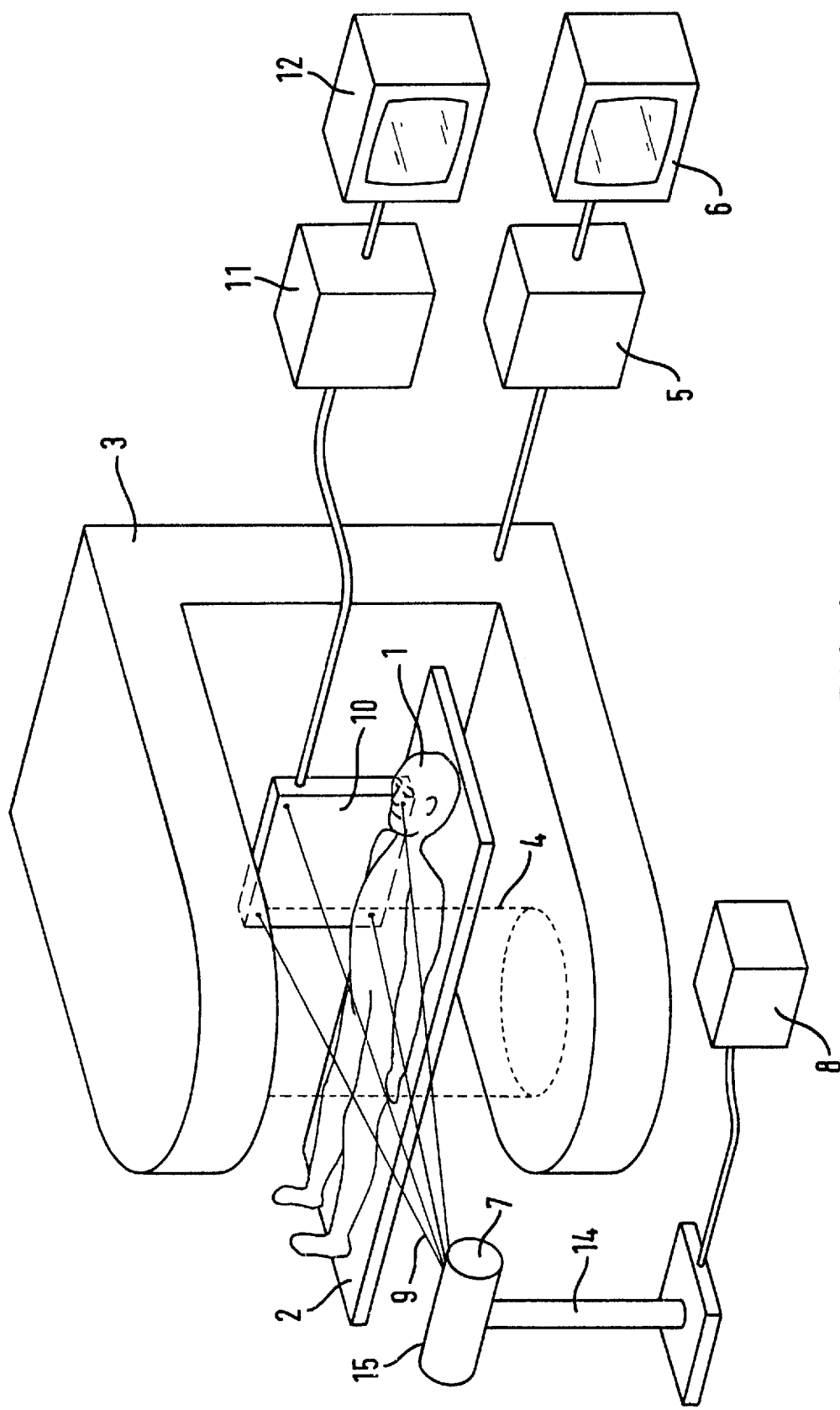
FIG. 1 is a perspective view of an embodiment of an examination installation of the invention.
Figure 2:
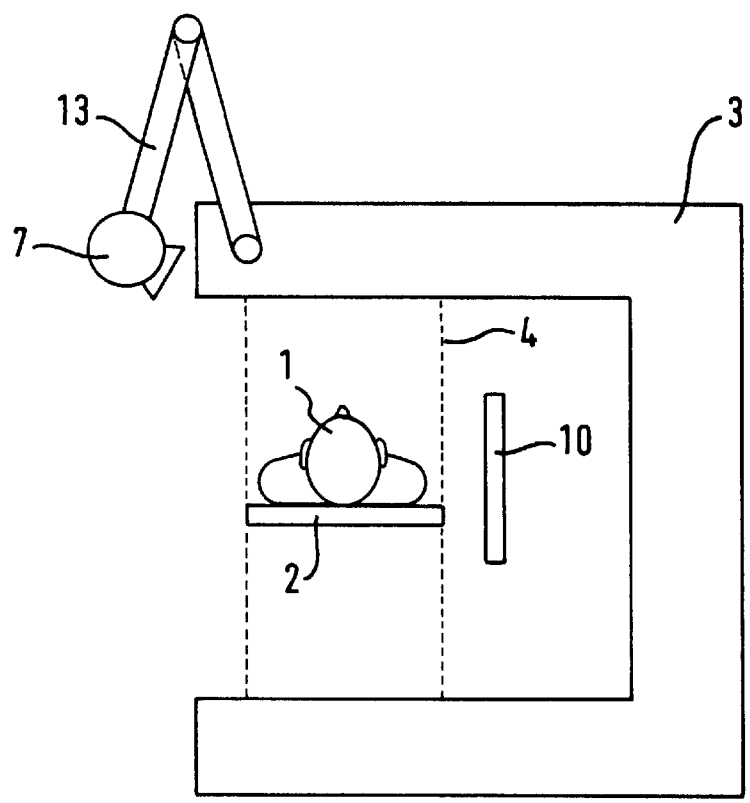
FIGS. 2–3 respectively show views of the examination installation according to FIG. 1 with the X-ray source in two different positions.
Figure 3:
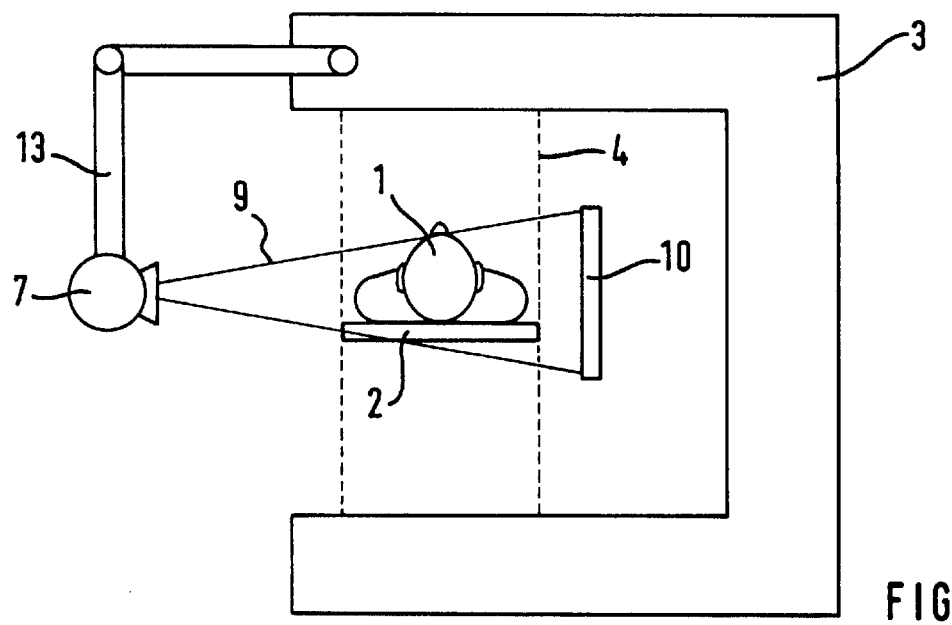

FIGS. 1 through 3 shows a patient lying on a patient support 2 and situated in a laterally open MR apparatus 3 for the production of MR exposures. The volume examined by the magnetic resonance is referenced 4. Lateral access to the patient 1 for manipulations is possible due to the laterally open MR apparatus 3. The processing of the MR signals ensues in a known manner in image electronics 5, and the MR images are reproduced on a monitor 6.

An X-ray source 7, which is supplied and controlled by a high-voltage generator 8, is provided for the production of X-ray exposures. The X-ray beam 9 emitted by the X-ray source 7 is gated into a pyramid shape and strikes a detector 10 that is formed of a matrix of detector elements. Each detector element can be formed of a photodiode and a preceding scintillator, with the scintillator converting the X-radiation into visible light and the photodiode converting the visible light into a corresponding electrical signal. The output signals of the detector elements of the detector 10 are supplied to image electronics 11 to which the monitor 12 for the playback of the X-ray images is connected.

In the illustrated medical diagnostics installation it is possible to produce X-ray images and MR images simultaneously in real time. These images can be reproduced on the two separate monitors 6 and 12 but can also be superimposed on one monitor.

The important feature is that the patient 1 can be simultaneously charged with the magnetic fields of the MR apparatus 3 and transirradiated by the X-ray beam 9, so that the described, simultaneous image generation ensues.

FIG. 1 shows that the X-ray source 7 is arranged on a floor stand 14 separated from the MR apparatus 3 at an adequate distance therefrom. The X-ray source 7 can be moved on the floor with the assistance of the floor stand 14 and can be placed into a standby position when it is not being used. When it is in use, the beam path is cleared. The influence of the magnetic field of the MR apparatus 3 on the X-ray source 7 is slight as a result.

This influence can be additionally reduced by the use of suitable cladding 15 on the X-ray source 7, the cladding 15 being a material that shields the magnetic field.

FIGS. 2 and 3 show an embodiment wherein the X-ray source 7 is pivotably connected to the upper leg of the MR apparatus 3 via an articulated arm 13. As a result, the X-ray source 7 according to FIG. 2 can be placed into a standby position or into a working position according to FIG. 3.

Although various changes and modifications to the presently preferred embodiments described herein will be apparent to those skilled in the art, such changes and modifications can be made without departing from the spirit and scope of the present invention and without diminishing its attendant advantages. Therefore, the appended claims are intended to cover such changes and modifications.

I claim as my invention:

1. A medical diagnostic apparatus comprising:
    means for producing a magnetic resonance image of a subject, including a patient support for supporting said subject while said MR image is obtained;
    an X-ray exposure system attached to said means for obtaining a magnetic resonance image, for obtaining an X-ray image of said subject simultaneously with said magnetic resonance image with said subject on said patient support without repositioning said subject.

2. A medical diagnostic apparatus as claimed in claim 1 wherein said X-ray exposure system includes an X-ray detector comprising a solid-state detector composed of a matrix of detector elements.

3. A medical diagnostic apparatus as claimed in claim 1 wherein said means for obtaining a magnetic resonance image comprises a laterally-open MR apparatus providing lateral access to said subject while on said patient support, and wherein said X-ray exposure system includes a radiation detector disposed opposite said lateral opening.

4. A medical diagnostic apparatus as claimed in claim 1 wherein said X-ray exposure system includes an X-ray source and means for mounting said X-ray source to said means for obtaining a magnetic resonance image for allowing positioning of said X-ray source between a standby position and an operating position for producing an X-ray exposure.

5. A medical diagnostic apparatus as claimed in claim 4 wherein said means for attaching said X-ray source to said means for obtaining a magnetic resonance image comprises an articulated arm extending between said X-ray source and said means for obtaining a magnetic resonance image.

6. A medical diagnostic apparatus as claimed in claim 1 wherein said X-ray exposure system includes an X-ray source, and a stand on which said X-ray source is mounted which is freely spatially adjustable.

7. A medical diagnostic apparatus as claimed in claim 1 wherein said X-ray exposure system includes an X-ray source, and cladding surrounding said X-ray source for shielding said X-ray source from magnetic fields produced by said means for obtaining a magnetic resonance image.

* * * * *